(12) United States Patent
Gladman et al.

(10) Patent No.: US 8,691,266 B2
(45) Date of Patent: Apr. 8, 2014

(54) WOUND DRESSING MATERIAL

(75) Inventors: June Michaela Gladman, Warrington (GB); Bryan Griffiths, Chester (GB)

(73) Assignee: Convatec Technologies, Inc., Las Vegas, NV (US)

( * ) Notice: Subject to any disclaimer, the term of this patent is extended or adjusted under 35 U.S.C. 154(b) by 1057 days.

(21) Appl. No.: 11/427,884

(22) Filed: Jun. 30, 2006

(65) Prior Publication Data

US 2007/0042024 A1 Feb. 22, 2007

(30) Foreign Application Priority Data

Jul. 1, 2005 (GB) .................................. 0513552.0

(51) Int. Cl.
*A61L 15/00* (2006.01)
(52) U.S. Cl.
USPC ............. 424/445; 442/50; 442/381; 442/383; 442/385; 442/402
(58) Field of Classification Search
USPC ........... 424/445; 602/41–47, 58; 428/76, 102, 428/170, 171
See application file for complete search history.

(56) References Cited

U.S. PATENT DOCUMENTS

| | | | | |
|---|---|---|---|---|
| 3,521,632 A | * | 7/1970 | Graham | 602/43 |
| 3,561,441 A | * | 2/1971 | Lombardi | 602/44 |
| 5,714,232 A | * | 2/1998 | Fenton et al. | 428/171 |
| 5,807,295 A | | 9/1998 | Hutcheon | |
| 6,268,544 B1 | * | 7/2001 | Court et al. | 602/41 |
| 7,745,681 B1 | * | 6/2010 | Ferguson | 602/43 |

FOREIGN PATENT DOCUMENTS

| | | |
|---|---|---|
| EP | 0642779 | 3/1995 |
| EP | WO 98/46818 | 10/1998 |
| GB | WO 93/12275 | 6/1993 |
| GB | WO 94/16746 | 8/1994 |
| GB | WO 00/01425 | 1/2000 |
| GB | WO 03/092755 | 11/2003 |
| WO | WO 93/11805 | 6/1993 |
| WO | WO9311805 | 6/1993 |
| WO | WO 94/17837 | 8/1994 |
| WO | WO9417837 | 8/1994 |

* cited by examiner

*Primary Examiner* — Michael G Hartley
*Assistant Examiner* — Jagadishwar Samala
(74) *Attorney, Agent, or Firm* — Wilson Sonsini Goodrich & Rosati

(57) ABSTRACT

A material for use as a wound dressing, the material being in the form of a roll and comprising gel forming fibers and the material having lines of longitudinal stitching.

5 Claims, 2 Drawing Sheets

WOUND DRESSING MATERIAL

This invention relates to a material suitable for forming into a wound dressing, in particular to bandages of the type in which the wound-contacting surface is composed of gel forming fibers in the form of a woven or non woven layer. In particular the invention relates to bandages comprising gel forming fibers used in the treatment of burns or skin graft sites.

BACKGROUND OF THE INVENTION

It is known to use carboxymethylated cellulosic materials in situations where a high degree of exudate absorption is required. For example, WO 93/12275 describes the production of various absorbent products capable of absorbing many times their own weight of water. This causes the carboxymethylated fibers to form a gel. WO 94/16746 and WO 00/01425 describe the use of carboxymethylated Lyocell materials in wound dressings where the advantages of gel formation in preventing adherence and, therefore, reducing wound damage and pain on removal are discussed.

Known wound dressings comprising gel forming fibers are essentially flat, rectangular and fairly small, typically 20 cm×15 cm. The usefulness of such dressings is limited in respect of large-scale wounds such as can occur on the chest or limbs due partly to the contraction of the dressing on gel formation and partly to the difficulty in maintaining close contact with the wound.

For example, wounds to an extensive area such as the chest or limb are presently treated using many overlapping patch type dressings. The contraction on the absorption of exudate is accommodated by overlapping the dressings. This then presents a problem in fixing the dressings and maintaining contact with the wound. Even if the dressings were made in larger sizes the problem of contraction would remain.

However, it would be desirable to bring the advantages of gel forming dressings to such burns by having the dressings available in bandage form. This is not, however, a simple matter. The current gel forming dressings, if presented in a strip form would contract, which, if allowed to occur unchecked, could apply compression to the burn. The patient's natural acute wound response is to cause a burned area to swell. Contraction of the dressing works against this response and is thus undesirable.

In addition, most gel forming dressings are made from non-woven fabrics. Such fabrics have poor integrity in tension. In applying a bandage it is often desirable to apply slight tension in order to obtain conformity between the bandage and the skin. This would not be possible with a bandage made from a non-woven fabric according to existing technology. The bandage when gelled may also not have sufficient integrity to maintain contact with the wound and may be difficult to remove in one piece.

The present invention, therefore, seeks to provide an improved material for use in wound dressings which mitigates the problems associated with patch dressings on extensive wounds.

SUMMARY OF THE INVENTION

We have now found that it is possible to restrict the contraction of dressings comprising gel forming fibers and improve their tensile strength in a dry and gelled state.

Accordingly, the invention provides a material for use as a wound dressing, the material being in the form of a roll and comprising gel forming fibers, the material having lines of longitudinal stitching.

The stitching is longitudinal in that it is generally parallel to the long dimension of the roll. The material is particularly suitable for forming bandages.

Such bandages are suited to dressing extensive areas as the bandage can be easily placed in intimate contact with the wound and surrounding skin. As the bandage can be applied under mild tension the bandage is maintained in contact with the wound. On absorption of exudate the gelled bandage is supported by the lines of stitching which are preferably made in nylon or polyolefin yarn or any yarn able to withstand gamma irradiation.

Preferably, the material comprises a wound contacting surface made from gel forming fibers and an outer surface made from textile fibers. In this manner the bandage has an inner layer which gels on contact with exudate and an outer layer which does not gel, but remains as a fabric much like a conventional secondary dressing. The stitching preferably passes through the whole thickness of the material. This has the advantage that the dressing may not require a secondary dressing to keep it in place and the outer textile layer gives the garment sufficient integrity to be removed from the wound in one piece without portions of the dressing being shed into the wound.

DETAILED DESCRIPTION OF THE INVENTION

Figure 1:
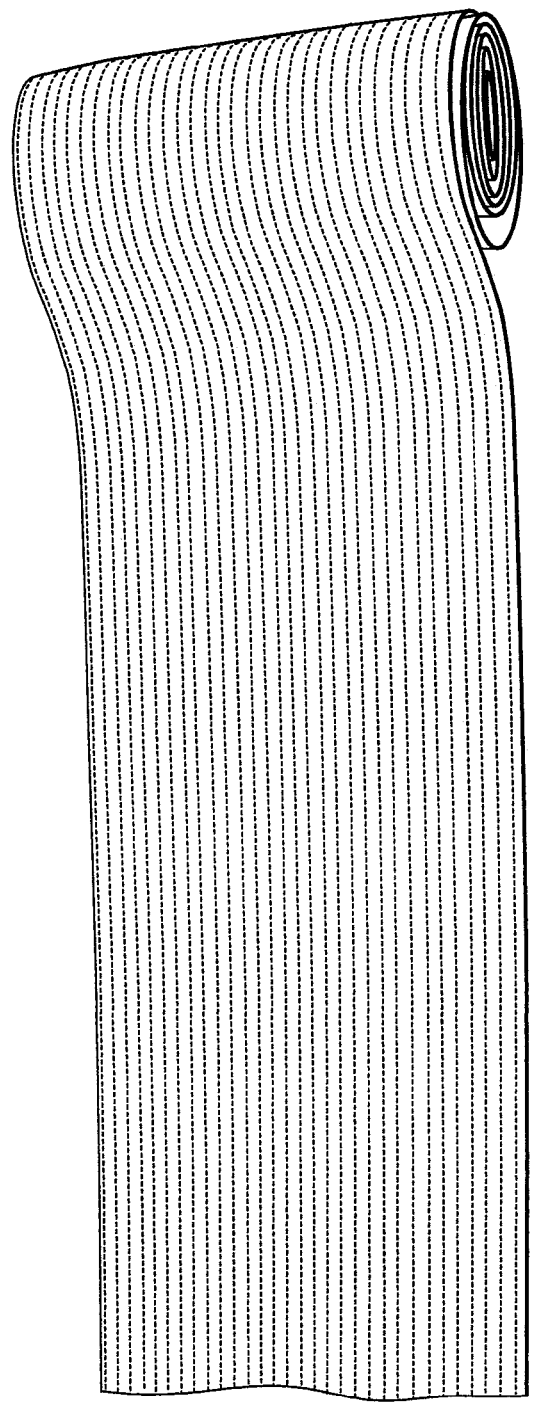
FIG. 1 is a view of a bandage made from woven gel forming fibers.

By gel forming fibers is meant hygroscopic fibers which upon the uptake of wound exudate become moist slippery or gelatinous and thus reduces the tendency for the surrounding fibers to adhere to the wound. The gel forming fibers can be of the type which retain their structural integrity on absorption of exudate or can be of the type which lose their fibrous form and become a structureless gel. The gel forming fibers are preferably spun sodium carboxymethylcellulose fibers, chemically modified cellulosic fibers, pectin fibers, alginate fibers, chitosan fibers, hyaluronic acid fibers, or other polysaccharide fibers or fibers derived from gums. The cellulosic fibers preferably have a degree of substitution of at least 0.05 carboxymethyl groups per glucose unit. The gel forming fibers preferably have an absorbency of at least 2 grams 0.9% saline solution per gram of fiber (as measured by the free swell method).

Preferably, the gel forming fibers have an absorbency of at least 10 g/g as measured in the free well absorbency method, more preferably between 15 g/g and 25 g/g.

The material may, for instance, comprise non-gel forming fibers and, in particular, may comprise lycra or other elastic fiber.

The material may be in the form of 1, 2 or more meter lengths and be approximately 30 cm wide. The lines of stitching may be from about 1 mm to about 10 mm apart and preferably from about 2 mm to about 5 mm apart. The lines of stitching are typically crocheted and have the appearance of a chain stitch, but other stitch patterns may also be used. Preferably, the lines of stitching are made with the fabric under slight tension so that a small amount of elongation of the material is possible. More preferably, the lines of stitching are made in a yarn which contracts on the application of heat. In this way, the bandage may be stitch bonded and then heated to contract the stitching. The bandage thus becomes slightly puckered which enables the bandage to elongate on application to the patient giving the advantage of close conformity with the wound. In general, elongation is limited to about 30% as it is not intended to apply compression with the bandage.

The bandage may further include one or more medicaments. For example, an antimicrobial agent, an antibiotic, an anesthetic, an anti-inflammatory agent, a skin protective agent or an odor absorbing agent or any combination thereof may be included.

Carboxymethylation can be achieved, for example, by sequential or simultaneous treatment of the cellulosic material with a strong alkali, such as aqueous sodium hydroxide, and monochloroacetic acid or a salt thereof. The appropriate reaction conditions will depend upon the composition of the fabric and the degree of carboxymethylation required and will be readily apparent to the person skilled in the art. They may be identical or similar to those described in WO 93/12275, WO 94/16746 or WO 00/01425 to which the reader is directed for further detail.

Preferably, the carboxymethylation is carried out in the presence of industrial methylated spirits (IMS), and IMS is, preferably, also used in a subsequent washing step, suitably along with water, as a cleaner and sterilizer. The degree of carboxymethylation is preferably such that upon absorption of exudate the fibers at the skin-contacting surface of the bandage form a gel.

A further aspect the invention provides a method of manufacturing a material for use as a wound dressing characterized in that the method comprises the steps of:
  (i) forming a roll of fabric comprising gel-forming fibers and
  (ii) stitching the roll with lines of longitudinal stitching.

Such a material is suitable for forming three dimensional garments preferably for use in the treatment of burns. It has been found that it is possible to cut shapes from the material and join those shapes together by stitching to form a three dimensional garment such as a glove for burns to the hand. An advantage of such garments is that they do not suffer contraction on gelling to the degree of known materials and, thus, do not constrict the burnt area. As it is possible to cut the garment, it can be tailored to the patient's needs. For example, with a glove, some of the fingers can be removed to allow visual inspection of the patient's fingers.

A further aspect the invention provides a three-dimensional garment formed from a material in the form of a roll, the roll comprising gel forming fibers, the material having lines of longitudinal stitching.

It has also been found that it is possible to cut lengths of the roll material and join those lengths together along their longitudinal edges, for example, by stitching, to increase the width of the material. Preferably, the lengths are overlapped slightly along their long edge and joined by stitching. In this way, a flat seam is made which does not irritate the wound. Joining lengths together allows relatively large shapes to be cut from the material, for example the parts needed to make a vest to cover the torso of a patient with burns to the chest.

FIG. 1 shows a knitted bandage incorporating lycra in the knit to give elongation. The stitch bonding can be seen in the form of lines of stitches along the length of the bandage.

Figure 2:
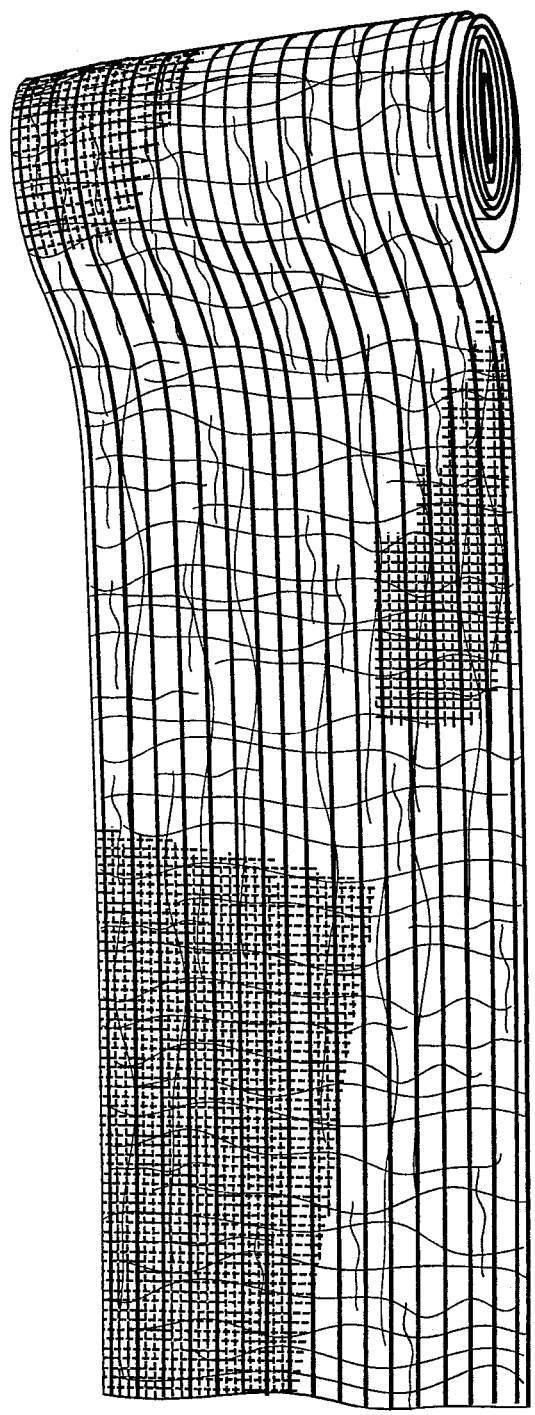
FIG. 2 is a view of a bandage made from non-woven gel forming fibers.

FIG. 2 shows a non-woven bandage made by forming a web of, for example, Lyocell which is then either hydroentangled or needlefelted. The web is then carboxymethylated by sequential or simultaneous treatment of the cellulosic material with a strong alkali, monochloroacetic acid or a salt thereof, and then stitch bonded to give elongation and strength to the bandage. Optionally, the bandage can have an antimicrobial material incorporated into it and, in particular, silver can be incorporated into it, for example by the method described in WO 02/43743.

Preferred embodiments of the invention are described with reference to the following examples:

EXAMPLE 1

A material in the form of a roll was made as described for the bandage of FIG. 2. A roll was also made in the same manner except that the stitch bonding was omitted. A dressing was cut from each roll of size 8 cm×8 cm and each was wetted with 7.5 mls of water. The gelled dressings were then measured to give the results below.

|  | Stitched Dressing ($cm^2$) | Unstitched Dressing ($cm^2$) |
| --- | --- | --- |
| Dry | 64 | 64 |
| Wet | 56.2 | 46.9 |

These results show the contraction of a dressing made from a small unstitched quantity of material. The dressing made from stitched material suffered far less contraction.

EXAMPLE 2

A roll of material was made by the method described for the material of FIG. 2. The roll of material was 20 cm wide and was cut into lengths 40 cm long. Those lengths were joined together at their long edges by overlapping the edges and stitching through both thicknesses. Shapes suitable for making garments were then cut from the material and sewn together to make three dimensional garments, such as gloves, vests and face masks, particularly, for use on burns.

The invention claimed is:

1. A material for use in a wound dressing, the material being in the form of a roll and consisting essentially of gel forming fibers and optionally elastic fibers, the gel forming fibers being in the form of a non-woven mat, and the material having lines of longitudinal stitching made in nylon or polyolefin yarn, and wherein the lines of stitching restrict the contraction of the dressing on absorption of exudates and increase the strength of the wound dressing.

2. The material as claimed in claim 1 wherein the lines of stitching are from about 1 mm to about 10 mm apart and are parallel to a long edge of the material.

3. The material as claimed in claim 1 wherein the gel forming fibers are selected from the group consisting of spun cellulose fibers, chemically modified cellulosic fibers, pectin fibers, alginate fibers, chitosan fibers, hyaluronic acid fibers, other polysaccharide fibers, fibers derived from gums and mixture thereof.

4. The material as claimed in claim 1 wherein the material comprises more than one layer and a wound contacting layer comprises gel forming fibers.

5. The material as claimed in claim 1 wherein the stitching is through the whole thickness of the material.

* * * * *